US007659059B2

(12) United States Patent
Troesch et al.

(10) Patent No.: US 7,659,059 B2
(45) Date of Patent: Feb. 9, 2010

(54) **METHOD FOR DETECTING AND/OR IDENTIFYING BACTERIA OF THE GENUS *STAPHYLOCOCCUS***

(75) Inventors: Alain Troesch, Genas (FR); Bruno Lacroix, Saint-Genis Laval (FR); Corinne Jay, Caluire (FR)

(73) Assignee: Biomerieux, Marcy l'Etoile (FR)

( * ) Notice: Subject to any disclaimer, the term of this patent is extended or adjusted under 35 U.S.C. 154(b) by 481 days.

(21) Appl. No.: 10/560,433

(22) PCT Filed: Jul. 8, 2004

(86) PCT No.: PCT/FR2004/050315

§ 371 (c)(1),
(2), (4) Date: Dec. 14, 2005

(87) PCT Pub. No.: WO2005/007883

PCT Pub. Date: Jan. 27, 2005

(65) Prior Publication Data

US 2007/0292846 A1   Dec. 20, 2007

(30) Foreign Application Priority Data

Jul. 10, 2003   (FR) .................................. 03 08446

(51) Int. Cl.
*C12Q 1/68* (2006.01)
(52) U.S. Cl. ......................................................... 435/6
(58) Field of Classification Search ........................ None
See application file for complete search history.

(56) References Cited

U.S. PATENT DOCUMENTS

| 4,672,040 A | 6/1987 | Josephson |
| 4,683,195 A | 7/1987 | Mullis et al. |
| 4,683,202 A | 7/1987 | Mullis |
| 4,800,159 A | 1/1989 | Mullis et al. |
| 4,981,783 A | 1/1991 | Augenlicht |
| 5,234,809 A | 8/1993 | Boom et al. |
| 5,399,491 A | 3/1995 | Kacian et al. |
| 5,445,934 A | 8/1995 | Fodor et al. |
| 5,695,926 A | 12/1997 | Cros et al. |
| 5,700,637 A | 12/1997 | Southern |
| 5,714,321 A | 2/1998 | Hogan |
| 5,744,305 A | 4/1998 | Fodor et al. |
| 5,750,338 A | 5/1998 | Collins et al. |
| 5,807,522 A | 9/1998 | Brown et al. |
| 6,133,047 A | 10/2000 | Elaissari et al. |
| 6,521,341 B1 | 2/2003 | Elaissari et al. |
| 6,632,662 B1 | 10/2003 | Broyer et al. |
| 2002/0187500 A1 | 12/2002 | Laayoun |

FOREIGN PATENT DOCUMENTS

| EP | 0 201 184 A2 | 12/1986 |
| EP | 0786519 | * 7/1997 |
| FR | 2 780 059 A1 | 12/1999 |
| JP | 06-090798 | 4/1994 |
| JP | A-2001-095579 | 4/2001 |
| JP | A-2002-051783 | 2/2002 |
| WO | WO 90/01069 A1 | 2/1990 |
| WO | WO 90/06995 A1 | 6/1990 |
| WO | WO 91/02818 A1 | 3/1991 |
| WO | WO 91/19812 A1 | 12/1991 |
| WO | WO 94/12670 A2 | 6/1994 |
| WO | WO 97/45202 A1 | 12/1997 |
| WO | WO 99/15321 A1 | 4/1999 |
| WO | WO 99/35500 A1 | 7/1999 |
| WO | WO 99/53304 A1 | 10/1999 |
| WO | WO 00/05338 A1 | 2/2000 |
| WO | WO 00/66788 | 11/2000 |
| WO | WO0134809 A2 * | 5/2001 |
| WO | WO 02/08265 A2 | 1/2002 |

OTHER PUBLICATIONS

Sambrook et al. Molecular cloning: A Laboratory Manual 1st edition, 1989.*
A.C. Whelen and David H. Persing, (1996) "The Role of Nucleic Acid Amplification and Detection in the Clinical Microbiology Laboratory"; 50, pp. 349-373.
J.M. Hunt and D. H. Persing, (1993) "Bacterial Detection"; $2^{ND}$ Edition, Section 13, pp. 525-555.
P.E. Nielsen et al. (1991) "Sequence-Selective Recognition of DNA by Strand Displacement With a Thymine-Substituted Polyamide"; 254, pp. 1497-1500.
R. Boom et al. (1990) "Rapid and Simple Method for Purification of Nucleic Acids", No. 28(3). pp. 495-503.

(Continued)

*Primary Examiner*—Robert B Mondesi
*Assistant Examiner*—Nina A Archie
(74) *Attorney, Agent, or Firm*—Oliff & Berridge, PLC

(57) ABSTRACT

The present invention relates to a method for detecting and/or identifying bacteria of the genus *Staphylococcus*, comprising the following steps:

Figure 1:
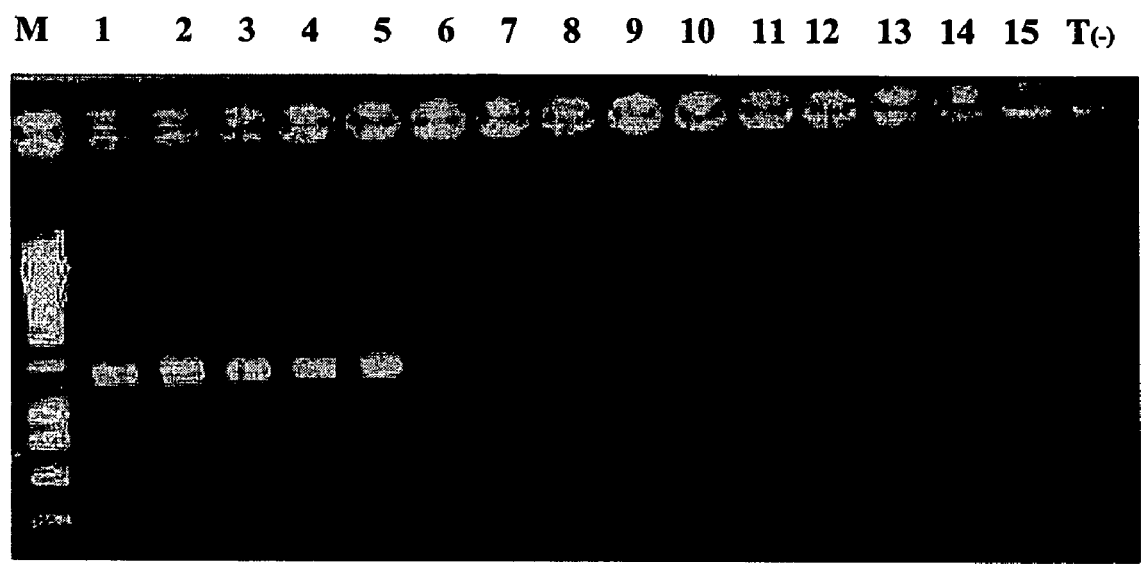

A. the nucleic acid material of the bacteria of the genus *Staphylococcus* is extracted, B. at least one target sequence of the nucleic acid material of the bacteria of the genus *Staphylococcus* is amplified using at least one amplification primer comprising at least 10 nucleotide motifs of SEQ ID No. 1 and/or at least one amplification primer comprising at least 10 nucleotide motifs of SEQ ID No. 2, in order to obtain amplicons of the target sequence, C. the presence of bacteria of the genus *Staphylococcus* is determined by detecting said amplicons.

1 Claim, 1 Drawing Sheet

OTHER PUBLICATIONS

P.R. Levison et al. (1998) "New Approaches to the Isolation of DNA by Ion-Exchange Chromatography"; Journal of Chromatography A. 827 pp. 337-344.

W. Ludwig et al. (1992) "Complete 23S Ribosomal RNA Sequences of Gram-Positive Bacteria With a Low DNA G+C Content"; Syst. Appl. Microbial. 15, pp. 487-501.

Larry Kricka (1999) "Nucleic Acid Detection Technologies—Labels, Strategies, and Formats"; Clinical Chemistry 45(4), pp. 453-458.

G.H. Keller et al. (1993) "Non-Radioactive Labeling Procedures" DNA Probes. $2^{nd}$ Edition, Sections 5 and 6, pp. 173-249.

Mark Chee et al. (1996) "Accessing Genetic Information With High-Density DNA Arrays"; Science Magazine, vol. 274, pp. 610-614.

A.C. Pease et al. (1994) "Light-Generated Oligonucleotide Arrays for Rapid DNA Sequence Analysis"; Proc. Natl. Acad. Sci. vol. 91, pp. 5022-5026.

G, Ramsay (1998) "DNA Chips: State-of-the-Art" Nature Biotechnology, vol. 16, pp. 40-44.

Frederic Ginot (1997) "Oligonucleotide Micro-Arrays for Identification of Unknown Mutations: How Far From Reality?" Human Mutation, No. 10, pp. 1-10.

Jing Cheng et al. (1996) "Microchip-Based Devices for Molecular Diagnosis of Genetic Diseases" Molecular Diagnosis vol. 1 No. 3 1996, pp. 183-200.

Tierry Livache et al. (1994) "Preparation of a DNA Matrix Via an Electrochemically Directed Copolymerization of Pyrrole and Oligonucleotides Bearing a Pyrrole Group"; Nucleic Acids Research, vol. 22, No. 15 pp. 2915-2921.

Jing Cheng et al. (1998) "Preparation and Hybridization Analysis of DNA/RNA From *E. Coli* on Microfabricated Bioelectronic Chips"; Nature Biotechnology, vol. 16, pp. 541-546.

F.J. Schmitz et al. (1997) "Specific Information Concerning Taxonomy, Pathogenicity and Methicillin Resistance of *Staphylococci*Obtained by a Multiplex PCR"; J. Med. Microbiol, vol. 46, pp. 773-778.

K.J. Edwards et al. (2001) "Rapid and Accurate Identification of Coagulase-Negative *Staphylococci* by Real-Time PCR"; Journal of Clinical Microbiology, vol. 39, No. 9, pp. 3047-3051.

William Mason et al. (2001) "Multiplex PCR Protocol for the Diagnosis of *Staphylococcal* Infection"; Journal of Clinical Microbiology, vol. 39, No. 9, pp. 3332-3338.

\* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Staphylococcus sp.

<400> SEQUENCE: 1
taacctacct ataagactgg                                        20

<210> SEQ ID NO 2
<211> LENGTH: 20
<212> TYPE: DNA
<213> ORGANISM: Staphylococcus sp.

<400> SEQUENCE: 2
tcaccccaat catttgtccc                                        20

METHOD FOR DETECTING AND/OR IDENTIFYING BACTERIA OF THE GENUS *STAPHYLOCOCCUS*

The present invention relates to the detection and/or identification of bacteria of the genus *Staphylococcus*.

The bacteria of the genus *Staphylococcus*, or staphylococci, are responsible for a large number of nosocomial infections and constitute a significant hospital problem. These bacteria are Gram-positive bacteria which can be classified into two large groups which are differentiated on the basis of the production of an enzyme, i.e. coagulase, which triggers coagulation of the plasma. Thus, a distinction is made between coagulase-negative staphylococci, the main representative of which is *Staphylococcus epidermidis*, and coagulase-positive staphylococci, the main representative of which is *Staphylococcus aureus*, whose virulence is well known. The staphylococci are widely distributed in the environment, the skin and the mucous membranes of man and animals. The regular desquamation of these hosts has the effect of dispersing the bacteria copiously in nature (water, soil, air, food and objects) and, in a hospital environment, draconian measures of hygiene and for the isolation of patients are required in order to limit dissemination of the epidermal strains. Thus, *Staphylococcus aureus*, which accounts for 80 to 90% of the staphylococci which are isolated clinically, is a major pathogen of man which is responsible for a large number of infections in a hospital environment, such as, in particular, nosocomial pneumonias, infections of surgical wounds, infections of burns, infections of foreign bodies (cardiac valves, hip prostheses, skin clips, etc.) and systemic infections, or for septicemias which are frequently due to using intravascular catheters or to the dissemination of the bacterium from another site of infection. While other staphylococci, such as *Staphylococcus epidermidis*, belong naturally to the human mucocutaneous flora, they also possess a pathogenic potential which is then expressed in a specific context: e.g. implantation of foreign bodies (cardiac prostheses, probes, catheters, etc.) and/or immunodeficiency (AIDS, radiotherapy, chemotherapy, the new-born state, etc.).

It thus turns out that any *staphylococcus* which is permanently colonizing the human skin and mucous membranes constitutes an infectious risk. It therefore proves to be essential to diagnose the presence of these bacteria at an early stage and to identify them.

Because of the very characteristic morphology of the Gram-positive bacteria, an initial microscopic examination makes it rapidly possible to suspect that staphylococci may be present in a biological sample, such as a blood sample or a sample which is derived from an infected wound.

If this microscopic examination shows that Gram-positive bacteria are present, a more detailed examination should be carried out in order, on the one hand, to confirm that these bacteria do indeed belong to the genus *Staphylococcus* and to ensure that the Gram-positive bacteria are not of another genus, such as bacteria of the genus *Micrococcus*, and, on the other hand, to identify the species (*Staphylococcus epidermis, aureus*, etc.) to which these bacteria belong. For this, the bacteria are cultured (on standard medium and Chapman's selective medium) and the following are carried out:

- a diagnosis of the genus to which these bacteria belong. This diagnosis of the genus can be achieved by means of a test of sensitivity to lysostaphin, to lysozyme or to nitrofurantoin,
- a diagnosis of the species to which these bacteria belong, which diagnosis can be effected using identification galleries, in particular.

The techniques of molecular biology are also used for diagnosing the genus and the species and enable a diagnosis to be made rapidly. The principle by which these techniques function is in the main based on one of the fundamentals of molecular biology, i.e. the phenomenon of hybridization (see, for example, A. C. Whelen and D. Persing, Annu. Rev. Microbiol., 1996, 50, p 349-373; J. M. Hunt and D. H. Persing, "Bacteria detection" in DNA Probes, ed G H Keller and M M Macrak, Stockton Press, $2^{nd}$ edition, Section 13, p 525-55).

The species and/or the genus can be diagnosed using hybridization probes. When the genomes of the different species of the bacteria of the genus *Staphylococcus* are compared, it is possible to discern what are termed conserved regions, whose sequences are identical in the different bacterial species of the genus *Staphylococcus* (these will subsequently be referred to as being "conserved target sequences"), and what are termed specific regions, whose sequences vary between the different bacterial species of the genus *Staphylococcus* and which are characteristic for each species (these will subsequently be referred to as being "specific target sequences"). When it is desired to diagnose a species, a hybridization probe which is specific for a given species, and which hybridizes as a result of complementarity to a specific target sequence, is chosen. When it is desired to diagnose a genus, a hybridization probe which is specific for the genus *Staphylococcus*, and which hybridizes, as a result of complementarity, to a conserved target sequence, is chosen. These molecular biological techniques having recourse to hybridization probes are well known to the skilled person, who can refer, in particular, to a source book such as "Molecular cloning, a laboratory manual", see, in particular, chapter 9: "analysis and cloning of eukaryotic genomic DNA" and paragraph 9.47: "Hybridization of radiolabeled probes to immobilized nucleic acids"; J Sambrook, E F Fritsch, T Maniatis, (eds Cold Spring Harbor Laboratory Press).

However, since the quantity of bacteria is generally too low in most clinical samples, it is frequently necessary to use an enzymic amplification reaction to increase the quantity of (conserved or specific) target sequences which are capable of hybridizing with a hybridization probe, in order to increase the probability of hybridization taking place between this target sequence and this hybridization probe. Such techniques are well known to the skilled person and mention may be made, in particular, of PCR (polymerase chain reaction), as described in the patents U.S. Pat. Nos. 4,683,195, 4,683,202 and 4,800,159.

This step of amplification for the purpose of diagnosing bacteria of the genus *Staphylococcus* is a tricky one since, not knowing either the species or the genera of bacteria which are capable of contaminating the sample, use should be made of amplification primers which exclusively amplify target sequences of bacteria of the genus *Staphylococcus*, with this amplification being effected whatever the species of the Staphylococcal bacteria might be. Furthermore, due to the high degree of variability of the genome between the different bacterial species belonging to the genus *Staphylococcus*, an amplification primer complying with the known sequence of one species of the genus *Staphylococcus* may fail to amplify another species of the genus *Staphylococcus*. The choice of the amplification primers is therefore crucial.

More precisely, the present invention provides novel amplification primers which facilitate the detection and/or identification of a large number of bacterial species belonging to the genus *Staphylococcus*. When the staphylococcal species which is present in a sample is unknown, it is then very pertinent to use primers according to the invention, which primers enable all the species of the genus *Staphylococcus* to be amplified. A large quantity of biological material is then obtained, with this subsequently making it possible to use a battery of specific probes to determine, without making any prior assumptions, the staphylococcal species which is present in the sample.

Surprisingly, the inventors have discovered that the amplification primers comprising the SEQ ID No. 1 (5' TAA CCT ACC TAT AAG ACTG G 3') or the SEQ ID No. 2 (5' TC ACC CCA ATC ATT TGT CCC 3') are very relevant for amplifying target sequences which make it possible not only to detect bacteria of the genus *Staphylococcus* but also to identify a large number of bacterial species belonging to the genus *Staphylococcus*.

In this regard, the invention relates to a method for detecting and/or identifying bacteria of the genus *Staphylococcus* in a biological sample, with the method comprising the following steps:
  A. the nucleic acid material of the bacteria of the genus *Staphylococcus* is extracted,
  B. at least one target sequence of the nucleic acid material of the bacteria of the genus *Staphylococcus* is amplified using at least one amplification primer comprising at least 10, preferably at least 15, and even more preferably at least 20, nucleotide motifs of SEQ ID No. 1 and/or at least one amplification primer comprising at least 10, preferably at least 15, and even more preferably at least 20, nucleotide motifs of SEQ ID No. 2, in order to obtain amplicons of the target sequence.
  C. the presence of bacteria of the genus *Staphylococcus* is determined by detecting said amplicons.

Within the meaning of the present invention, the bacteria of the genus *Staphylococcus* can, in particular, be *Staphylococcus arlettae; Staphylococcus aureus.aureus; Staphylococcus auricularis; Staphylococcus capitis.capitis; Staphylococcus capitis.ureolyticus; Staphylococcus caprae; Staphylococcus carnosus carnosus; Staphylococcus carnosus utilis; Staphylococcus chromogenes; Staphylococcus cohnii cohnii; Staphylococcus cohnii urealyticum; Staphylococcus condimenti; Staphylococcus delphini; Staphylococcus epidermidis; Staphylococcus equorum; Staphylococcus gallinarum; Staphylococcus haemolyticus; Staphylococcus hominis.hominis; Staphylococcus hominis.novobiosepticus; Staphylococcus hyicus; Staphylococcus intermedius; Staphylococcus kloosii; Staphylococcus lentus; Staphylococcus lugdunensis; Staphylococcus pasteuri; Staphylococcus piscifermentans; Staphylococcus pulvereri; Staphylococcus saprophyticus.bovis; Staphylococcus saprophyticus.saprophyticus; Staphylococcus schleiferi.coagulans; Staphylococcus schleiferi.schleiferi; Staphylococcus sciuri; Staphylococcus simulans; Staphylococcus vitulinus; Staphylococcus warneri* and *Staphylococcus xylosus* bacteria.

Within the meaning of the present invention, a biological sample is understood as being any sample which may possibly contain a nucleic acid material as defined below. This biological sample can be taken from a patient and can, in particular, be a sample of infected tissues, or nasal, blood, serum, saliva or circulating cell samples taken from the patient. This biological sample is taken by any means known to the skilled person. This biological sample can also be a food sample, a sample of water, of milk or of food of animal origin or a sample taken in a veterinary context (infected tissues, etc.).

Within the meaning of the present invention, the nucleic acid material comprises a nucleic acid sequence such as a deoxyribonucleic acid (DNA) sequence or a ribonucleic acid (RNA) sequence. A nucleic acid sequence (or nucleotide, oligonucleotide or polynucleotide fragment) is understood as being a chain of nucleotide motifs which are linked to each other by phosphoric ester bonds, which chain is characterized by the informational sequence of the natural nucleic acids, which are capable of hybridizing with another sequence of nucleic acids, and with the chain being able to contain monomers of different structures and to be obtained from a natural nucleic acid molecule and/or by means of genetic recombination and/or by means of chemical synthesis. A nucleic acid motif is understood as being a derivative of a monomer which can be a natural nucleic acid nucleotide, the constitutive elements of which are a sugar, a phosphate group and a nitrogen base; the sugar is 2-deoxy-ribose in DNA while it is ribose in RNA; depending on whether the nucleic acid is DNA or RNA, the nitrogen base is selected from adenine, guanine, uracil, cytosine and thymine; or else the monomer is a nucleotide at least one of whose three constitutive elements has been modified; by way of example, the modification can take place at the level of the bases, using modified bases such as inosine, 5-methyl-deoxycytidine, deoxyuridine, 5-dimethylamino-deoxyuridine, 2,6-diamino-purine, 5-bromo-deoxyuridine or any other modified base which is capable of hybridization, at the level of the sugar, for example with at least one deoxyribose being replaced with a polyamide (P. E. Nielsen et al, Science, 254, 1497-1500 (1991), or else at the level of the phosphate group, for example with this group being replaced with esters which are selected, in particular, from diphosphates, alkylphosphonates, arylphosphonates and phosphorothioates.

According to a preferred embodiment of the invention, the nucleic acid material comprises a deoxyribonucleic acid sequence.

This nucleic acid sequence comprises at least one target sequence. A target sequence is understood as being a sequence the order of whose nucleotide motifs makes it possible to determine the presence of a bacterium of the genus *Staphylococcus* and/or to identify the bacterial species belonging to the genus *Staphylococcus*. This target sequence comprises at least one conserved target sequence, that is to say a sequence the order of whose nucleotide motifs makes it possible to determine the presence of any bacterial species belonging to the genus *Staphylococcus*. The target sequence can additionally comprise at least one specific target sequence, that is to say a sequence the order of whose nucleotide motifs makes it possible to identify a given bacterial species belonging to the genus *Staphylococcus*. According to an even more preferred embodiment of the invention, the specific target sequence is included between two conserved target sequences.

According to a preferred embodiment of the invention, the nucleic acid material is extracted from a biological sample which has been taken from a patient.

Within the meaning of the present invention, an amplification primer is understood as being a nucleic acid sequence which comprises from 5 to 100 nucleotide motifs, preferably from 15 to 25 nucleotide motifs, which sequence makes it possible to initiate an enzymic polymerization such as, in particular, an enzymic amplification reaction. This amplification primer comprises at least 10, preferably 15, and even more preferably 20, nucleotide motifs of SEQ ID No. 1 or at least 10, preferably 15, and even more preferably 20, nucleotide motifs of SEQ ID No. 2. Within the meaning of the present invention, an amplification primer comprising
  a sequence which is homologous with SEQ ID No. 1 or SEQ ID No. 2, that is to say
    the sequence which is complementary to, or sufficiently complementary to, SEQ ID No. 1 or 2 a sequence which exhibits a homology which is sufficient for hybridizing with SEQ ID No. 1 or SEQ ID No. 2 or with the sequence which is complementary to SEQ ID No. 1 or SEQ ID No. 2, a sequence which comprises a sequence of SEQ ID No. 1 or SEQ ID No. 2 (or a sequence which is homologous with SEQ ID No. 1 or SEQ ID No. 2 as previously defined) in which the thymine bases are replaced with uracil bases, and, which would have the same function as the amplification primer according to the invention, that is to say enable a large number of bacterial species belonging to the genus *Staphylococcus* to by amplified, is regarded as being equivalent to the amplification primer according to the invention.

An enzymic amplification reaction is understood as being a process which generates multiple copies (or amplicons) of a nucleic acid sequence as a result of the action of at least one enzyme. Such amplification reactions are well known to the skilled person and mention may be made, in particular, of PCR (polymerase chain reaction) as described in the patents U.S. Pat. Nos. 4,683,195, 4,683,202 and 4,800,159; LCR (ligase chain reaction), which is explained, for example, in the patent application EP-A-0 201 184; RCR (repair chain reaction), which is described in the patent application WO-A-90/01069; 3SR (self-sustained sequence replication), together with the patent application WO-A-90/06995; NASBA (nucleic acid sequence-based amplification), together with the patent application WO-A-91/02818, or else TMA (transcription-mediated amplification) together with the patent U.S. Pat. No. 5,399,491. In the remainder of the account, reference will be made to a target sequence whether it consists of a single strand or a double strand.

In step A the nucleic acid material is extracted using any protocol known to the skilled person. As a rough guide, the nucleic acids can be extracted by means of a step of lyzing the cells which are present in the biological sample in order to release the nucleic acids which are contained in the protein and/or lipid envelopes of the microorganisms (as cell debris which interferes with the subsequent reactions). By way of example, it is possible to use the lysis methods as described in the patent applications WO 00/05338, dealing with mixed magnetic and mechanical lysis, WO 99/53304 dealing with electrical lysis, and WO 99/15321 dealing with mechanical lysis.

The skilled person would be able to use other well known lysis methods such as thermal or osmotic shocks or chemical lyses using chaotropic agents such as guanidium salts (U.S. Pat. No. 5,234,809). This lysis step can also be followed by a purification step, with the latter enabling the nucleic acids to be separated from the other cellular constituents which are released in the lysis step. In general, this purification step enables the nucleic acids to be concentrated and can be adapted for purifying DNA or RNA. By way of example, it is possible to use magnetic particles which may possibly be coated, by means of adsorption or covalence, with oligonucleotides (in this regard, see the patents U.S. Pat. Nos. 4,672,040 and 5,750,338), and thus to purify the nucleic acids, which have attached themselves to these magnetic particles, by means of a washing step. This step of purifying the nucleic acids is particularly advantageous if it is desired to subsequently amplify said nucleic acids. A particularly advantageous method of creating these magnetic particles is described in the patent applications WO 97/45202 and WO 99/35500. Another advantageous example of a method for purifying the nucleic acids is that of using silica either in the form of a column or in the form of inert particles (Boom R. et al., J. Clin. Microbiol., 1990, No. 28(3), p. 495-503) or magnetic particles (Merck: MagPrep® silica, Promega: MagneSil™ paramagnetic particles). Other widely used methods are based on ion exchange resins which are used in columns or in paramagnetic particle format (Whatman: DEAE-Magarose) (Levison P R et al., J. Chromatography, 1998, p. 337-344). Another method which is very relevant but is not exclusive for the invention is that of adsorption onto a metallic oxide support (Xtrana company: Xtra-Bind™ matrix).

When it is desired to specifically extract DNA from a biological sample, it is possible, in particular, to effect an extraction using phenol, chloroform and alcohol, in order to eliminate the proteins, and to precipitate the DNA with 100% alcohol. The DNA can then be pelleted by centrifugation, washed and resuspended.

In step B, at least one target sequence of the nucleic acid material is amplified using any one of the enzymic amplification reactions as previously defined. These techniques generally make use of a cyclic succession which comprises the following steps:

denaturation of the target sequence, if it is double stranded, in order to obtain two complementary target strands, hybridization of each of the target strands, which have been obtained in the preceding denaturation step, with at least one amplification primer, formation, starting with the amplification primers, of the strands which are complementary to the strands with which the primers are hybridized in the presence of a polymerase enzyme and nucleoside triphosphates (ribonucleoside triphosphate and/or deoxyribonucleoside triphosphate depending on the techniques employed)

with this cycle being repeated a predetermined number of times in order to obtain the target sequence in a proportion which is sufficient to enable it to be detected.

Hybridization is understood as being the process during which two nucleic acid sequences, such as, in particular, an amplification primer and a target sequence or a hybridization probe and a target sequence, bind together, under appropriate conditions, by means of stable and specific hydrogen bonds in order to form a double strand. These hydrogen bonds are formed between the complementary bases adenine (A) and thymine (T) (or uracil (U)) (reference is made to an A-T bond) or between the complementary bases guanine (G) and cytosine (C) (reference is made to a G-C bond). The hybridization of two nucleic acid sequences can be total (reference is then made to complementary sequences), that is to say the double strand which is obtained in this hybridization is composed solely of A-T bonds and C-G bonds. This hybridization can be partial (reference is then made to sufficiently complementary sequences), that is to say that, while the double strand which is obtained comprises A-T bonds and C-G bonds which enable the double strand to be formed, it also contains bases which are not linked to a complementary base. The hybridization between two complementary or sufficiently complementary sequences depends on the operational conditions which are employed and, in particular, on the stringency. The stringency is defined, in particular, according to the base composition of the two nucleic acid sequences as well as by the degree of mispairing between these two nucleic acid sequences. The stringency can also vary according to the parameters of the reaction, such as the concentration and type of ionic species which are present in the hybridization solution, the nature and concentration of denaturing agents and/or the hybridization temperature. All these facts are well known, and the appropriate conditions can be determined by the skilled person. In general, depending on the length of the nucleic acid sequences which it is desired to hybridize, the hybridization temperature is between approximately 20 and 70° C., in particular between 35 and 65° C., in a saline solution whose concentration is from approximately 0.5 to 1 M. In the hybridization step, the amplification primer according to the invention preferably hybridizes with a conserved target sequence.

According to a preferred embodiment of the invention, at least one target sequence is amplified by means of PCR. This amplification reaction can be carried out by the hybridization of two amplification primers, which hybridize to each end of the target sequence which it is desired to amplify. Each amplification primer preferably hybridizes with a conserved target sequence. As a rough guide, when an amplification primer comprising 20 nucleotide motifs of SEQ ID No. 1 and an amplification primer comprising 20 nucleotide motifs of SEQ ID No. 2 are used, a target sequence having a size of 1375 base pairs is amplified. This target sequence would correspond, for example, to the sequence 128-1503 of the *Staphylococcus aureus* genome (Genbank reference X68417). This sequence is then very relevant for identifying bacterial species belonging to the genus *Staphylococcus* since a length of 1375 base pairs makes it possible to obtain, within this long sequence, a large number of regions which are specific for each Staphylococcal species, with each of the specific regions being able to be identified by using a battery of species probes.

According to a preferred embodiment of the invention, when an amplification primer comprising 20 nucleotide motifs of SEQ ID No. 1 and an amplification primer comprising 20 nucleotide motifs of SEQ ID No. 2 are used in a PCR, each cycle of the enzymic amplification reaction comprises the following steps:

denaturation of the target sequence, if the latter is double-stranded (and/or denaturation of the target sequence and of the amplicon from the $2^{nd}$ cycle onwards), with this denaturation being preferably effected at a temperature of between 90 and 99° C., even more preferably of between 94 and 95° C., for a period which is preferably between 20 and 40 seconds, and even more preferably for a period of between 25 and 35 seconds, hybridization of each of the target strands, which were obtained in the preceding denaturation step, with at least one amplification primer, with this preferably being effected at a temperature of between 50 and 60° C., and even more preferably of between 53 and 57° C., for a period which is preferably of between 20 and 40 seconds and, still more preferably, for a period of between 25 and 35 seconds, formation, starting with the amplification primers, of copies of the target sequence (or amplicons), with this preferably being effected at a temperature of between 65 and 80° C., and even more preferably of between 70 and 74° C., for a period which is preferably of between 45 and 75 seconds, and even more preferably for a period of between 55 and 65 seconds, with this cycle preferably being repeated from 25 to 35 times, and even more preferably 30 times.

Within the meaning of the present invention, amplicons are understood as being the copies of the target sequence which are obtained during an enzymic amplification reaction.

The detection of the amplicons in step C can be effected using any protocols known to the skilled person which relate to detecting nucleic acids. As a rough guide, this detection can be effected following the migration of the amplicons under the influence of electrophoresis, with the amplicons migrating in accordance with their size. The gel and the migration medium can contain ethidium bromide in order to enable the amplicons to be detected directly, by the emission of a luminous signal, when the gel is placed, after a given migration time, on a UV (ultraviolet) ray transilluminator. These electrophoresis techniques are well known to the skilled person. The amplicons can also be detected and quantified by using a quantification range which is obtained by means of an amplification reaction which is taken to saturation.

It is also possible to use hybridization probes for detecting the presence of the amplicons. Within the meaning of the present invention, a hybridization probe is understood as being a nucleic acid sequence which contains from 5 to 100 nucleotide motifs, in particular from 15 to 35 nucleotide motifs, and possesses a hybridization specificity, under predetermined conditions, for forming a hybridization complex with a target nucleic acid sequence. The hybridization probe can comprise a label for detecting it. The probe is then referred to as being a detection probe. Detection is understood as meaning either direct detection by means of a physical method or indirect detection by means of a detection method which uses a label. A large number of detection methods for detecting nucleic acids exist. [See, for example, Kricka et al., Clinical Chemistry, 1999, No. 45(4), p. 453-458 or Keller G. H. et al., DNA Probes, 2nd Ed., Stockton Press, 1993, sections 5 and 6, p. 173-249]. A label is understood as being a tracer which is able to engender a signal which can be detected. A nonlimiting list of these tracers comprises enzymes, such as horseradish peroxidase, alkaline phosphatase, beta-galactosidase and glucose 6-phosphate dehydrogenase, which produce a signal which can be detected, for example, by means of colorimetry, fluorescence or luminescence; chromophores such as fluorescent, luminescent or dye compounds; groups having an electron density which can be detected by means of electron microscopy or by means of their electrical properties such as conductivity, by means of amperometric or voltametric methods, or by means of impedance measurements; groups which can be detected by means of optical methods such as diffraction, surface plasmon resonance or contact angle variation, or by means of physical methods such as atomic force spectroscopy, the tunnel effect, etc.; and radioactive molecules such as $^{32}P$, $^{35}S$ or $^{125}I$.

According to one particular embodiment of the invention, the method as defined above additionally comprises the following step:

D. the bacterial species belonging to the genus *Staphylococcus* is identified by using at least one hybridization probe which is able to hybridize with a target sequence which is specific for a bacterial species belonging to the genus *Staphylococcus*.

A hybridization probe which is able to hybridize with a target sequence which is specific for a bacterial species belonging to the genus *Staphylococcus* is understood as being a hybridization probe which is as previously defined and which comprises at least one sequence which is complementary, or sufficiently complementary, to a target sequence which is specific for a bacterial species belonging to the genus *Staphylococcus*. Within the meaning of the present invention, the hybridization probe can be what is termed a detection probe. In this case, the so-called detection probe is labeled with a label as previously defined. Due to the presence of this label, it is possible to detect the presence of a hybridization reaction between a given detection probe and the target sequence which is specific for a given species. The presence of such a hybridization reaction thus makes it possible to identify a given bacterial species belonging to the genus *Staphylococcus*. The hybridization probe can also be what is termed a capture probe. In this case, the so-called capture probe is immobilized, or can be immobilized, on a solid support by any appropriate means, that is to say directly or indirectly, for example by means of covalence or adsorption. The hybridization reaction between a given capture probe and a target sequence which is specific for the given species is then detected, with this enabling the bacterial species to be identified. Preference is given to using target sequences which are labeled directly (in particular by incorporating a label into the target sequence) or indirectly (in particular by using a detection probe as previously defined) for detecting the hybridization reaction. It is possible, in particular, to carry out, prior to the hybridization step, a step of labeling, for example by using a deoxyribonucleotide triphosphate which is labeled during the enzymic amplification reaction, and/or of cleaving, the target sequence. The cleavage can be effected, in particular, by the action of imidazole and manganese chloride. The target sequence can also be labeled after the amplification step, for example by hybridizing a detection probe using the sandwich hybridization technique described in the document WO 91/19812. Another particular and preferred method of labeling nucleic acids is described in the application FR 2 780 059.

It is possible to use, as the solid support, synthetic materials or natural materials, which may possibly have been modified chemically, in particular polysaccharides such as cellulose-based materials, for example paper, cellulose derivatives such as cellulose acetate and nitrocellulose or dextran, polymers, copolymers, in particular based on monomers of the styrene type, natural fibers such as cotton, and synthetic fibers such as nylon; mineral materials such as silica, quartz, glasses and ceramics; latexes; magnetic particles; metallic derivatives, gels, etc. The solid support can be in the form of a microtitration plate, of a membrane as described in the application WO 94/12670, or of a particle. It is also possible to immobilize several different capture probes on the support, with each capture probe being specific for a bacterial species belonging to the genus *Staphylococcus*. According to a preferred embodiment of the invention, a biochip, on which a large number of different capture probes are immobilized, is used as the support. A biochip is understood as being a solid support of reduced size on which a multitude of capture probes are fixed at predetermined positions. The concept of a biochip, or DNA chip, dates from the beginning of the 1990s and is based on a multidisciplinary technology which integrates microelectronics, nucleic acid chemistry, image analysis and computing. As a rough guide, mention may be made of the DNA chips developed by the Affymetrix company ("Accessing Genetic Information with High-Density DNA arrays", M. Chee et al., Science, 1996, 274, 610-614; "Light-generated oligonucleotide arrays for rapid DNA sequence analysis", A. Caviani Pease et al., Proc. Natl. Acad. Sci. USA, 1994, 91, 5022-5026) for molecular diagnoses. Other examples of biochips are given in the publications by G. Ramsay, Nature Biotechnology, 1998, No. 16, p. 40-44; F. Ginot, Human Mutation, 1997, No. 10, p. 1-10; J. Cheng et al, Molecular diagnosis, 1996, No. 1(3), p. 183-200; T. Livache et al, Nucleic Acids Research, 1994, No. 22(15), p. 2915-2921; J. Cheng et al, Nature Biotechnology, 1998, No. 16, p. 541-546 or in the patents U.S. Pat. Nos. 4,981,783, 5,700,637, 5,445,934, 5,744,305 and 5,807,522. The main characteristic of the solid support should be to preserve the characteristics of the hybridization of the capture probes with the target sequences while at the same time generating a background which is a minimum for the detection method. The biochip method is based on using capture probes which are fixed on a solid support and on which target nucleic acid sequences, which are labeled directly or indirectly with fluorochromes, for example, are caused to react. The capture probes are located specifically on the support or chip and each hybridization gives a specific item of information in relation to the target nucleic acid sequence. Following hybridization, the support or chip is washed and the hybridization reaction between a labeled target nucleic acid sequence and a capture probe can be detected by using a high-affinity ligand which is linked, for example, to a label of the fluorochrome type. The fluorescence is read by a scanner, for example, and the analysis of the fluorescence is processed using a computer. The presence of a hybridization reaction between a given capture probe and a target sequence which is specific for a given species thus makes it possible to identify the given bacterial species belonging to the genus *Staphylococcus*.

The invention also relates to an amplification primer which is characterized in that it comprises at least 10, preferably at least 15, and even more preferably at least 20, nucleotide motifs of SEQ ID No. 1 and to an amplification primer which is characterized in that it comprises at least 10, preferably at least 15, and even more preferably at least 20, nucleotide motifs of SEQ ID No. 2.

The amplification primer according to the invention preferably comprises at least 10, preferably at least 15, and even more preferably at least 20, contiguous nucleotide motifs of SEQ ID No. 1 or at least 10, preferably at least 15, and even more preferably at least 20, contiguous nucleotide motifs of SEQ ID No. 2.

Within the meaning of the present invention, an amplification primer which comprises
  a sequence which is homologous to SEQ ID No. 1 or SEQ ID No. 2, that is to say
    the sequence which is complementary, or sufficiently complementary, to SEQ ID No. 1 or 2
    a sequence which exhibits 80% homology with SEQ ID No. 1 or SEQ ID No. 2,
  a sequence which comprises a sequence of SEQ ID No. 1 or SEQ ID No. 2 (or a sequence which is homologous to SEQ ID No. 1 or SEQ ID No. 2, as previously defined) in which the thymine bases are replaced with uracil bases, or in which at least one base is replaced with a universal base such as inosine, and which would have the same function as the amplification primer according to the invention, that is to say enable a large number of bacterial species belonging to the genus *Staphylococcus* to be amplified, is regarded as being equivalent to the amplification primer according to the invention.

The invention also relates to a pair of amplification primers, which pair is characterized in that it comprises an amplification primer which comprises at least 10, preferably at least 15, and even more preferably at least 20, nucleotide motifs of SEQ ID No. 1 and an amplification primer which comprises at least 10, preferably at least 15, and even more preferably at least 20, nucleotide motifs of SEQ ID No. 2. This primer pair is preferably used in an enzymic amplification reaction such as PCR.

The invention also relates to the use of at least one primer which comprises at least 10, preferably at least 15, and even more preferably at least 20, nucleotide motifs of SEQ ID No. 1 and/or at least one primer which comprises at least 10, preferably at least 15, and even more preferably at least 20, nucleotide motifs of SEQ ID No. 2 for detecting and/or identifying bacteria which belong to the genus *Staphylococcus*.

The invention finally relates to a kit for diagnosing bacteria of the genus *Staphylococcus*, which kit comprises at least one primer which comprises at least 10, preferably at least 15, and even more preferably at least 20, nucleotide motifs of SEQ ID No. 1 and/or at least one primer which comprises at least 10, preferably at least 15, and even more preferably at least 20, nucleotide motifs of SEQ ID No. 2.

The invention also relates to a hybridization probe which is characterized in that it comprises at least 10, preferably at least 15, and even more preferably at least 20, nucleotide motifs of SEQ ID No. 1, and to a hybridization probe which is characterized in that it comprises at least 10, preferably at least 15, and even more preferably at least 20, nucleotide motifs of SEQ ID No. 2.

Preferably, the hybridization probe according to the invention comprises at least 10, preferably at least 15, and even more preferably at least 20, contiguous nucleotide motifs of SEQ ID No. 1 or at least 10, preferably at least 15, and even more preferably at least 20, contiguous nucleotide motifs of SEQ ID No. 2.

Within the meaning of the present invention, a hybridization probe which comprises
- a sequence which is homologous to SEQ ID No. 1 or SEQ ID No. 2, that is to say
  - the sequence which is complementary, or sufficiently complementary, to SEQ ID No. 1 or 2,
  - a sequence which exhibits 80% homology with SEQ ID No. 1 or SEQ ID No. 2,
- a sequence which comprises a sequence of SEQ ID No. 1 or SEQ ID No. 2 (or a sequence which is homologous to SEQ ID No. 1 or SEQ ID No. 2, as previously defined) in which the thymine bases are replaced with uracil bases, or in which at least one base is replaced with a universal base such as inosine, and which would have the same function as the hybridization probe according to the invention, that is to say enable a large number of bacterial species belonging to the genus *Staphylococcus* to be detected, is regarded as being equivalent to the hybridization probe according to the invention.

The hybridization probe according to the invention can be a detection probe or a capture probe, as previously defined.

The invention also relates to the use of at least one hybridization probe which comprises at least 10, preferably at least 15, and even more preferably at least 20, nucleotide motifs of SEQ ID No. 1 and/or at least one hybridization probe which comprises at least 10, preferably at least 15, and even more preferably at least 20, nucleotide motifs of SEQ ID No. 2 for detecting and/or identifying bacteria which belong to the genus *Staphylococcus*.

The invention also relates to a kit for diagnosing bacteria of the genus *Staphylococcus*, which kit comprises at least one hybridization probe which comprises at least 10, preferably at least 15, and even more preferably at least 20, nucleotide motifs of SEQ ID No. 1 and/or at least one hybridization probe which comprises at least 10, preferably at least 15, and even more preferably at least 20, nucleotide motifs of SEQ ID No. 2.

Finally, the invention relates to a composition for detecting bacteria of the genus *Staphylococcus*, which composition comprises at least one hybridization probe which comprises at least 10, preferably at least 15, and even more preferably at least 20, nucleotide motifs of SEQ ID No. 1 and/or at least one hybridization probe which comprises at least 10, preferably at least 15, and even more preferably at least 20, nucleotide motifs of SEQ ID No. 2.

The following FIGURE is given by way of illustration and is in no way limiting. It will enable the invention to be better understood.

FIG. 1 shows a photograph of an electrophoresis gel as obtained after the migration of different amplicons, which were obtained as described in the following example and which were loaded in wells 1 to 15. The amplicons were derived from different bacterial species belonging to the genus *Staphylococcus* (well 1: *Staphylococcus cohnii* ssp *cohnii*; well 2: *Staphylococcus cohnii* ssp *urealyticum*; well 3: *Staphylococcus intermedius*; well 4: *Staphylococcus xylosus*; well 5: *Staphylococcus pasteuri*) and from bacterial species which did not belong to the genus *Staphylococcus* (well 6: *Streptococcus pneumoniae*; well 7: *Klebsiella pneumoniae*; well 8: *Pseudomonas aeruginosa*; well 9: *Enterococcus faecalis*; well 10: *Enterobacter cloacae*; well 11: *Proteus mirabilis*; well 12: *Streptococcus agalactiae*; well 13: *Citrobacter freundii*; well 14: *Salmonella enteritidis*; well 15: *Stenotrophomonas maltophila*). The fact that the amplicons were of the correct size was verified by the simultaneous migration of a size marker (well M). The presence of bacteria of the genus *Staphylococcus* was confirmed by the presence of a band which was of the expected size and which corresponded to an amplicon of approximately 1.4 kB (wells 1 to 5), whereas no band was observed in the case of the bacteria which did not belong to the genus *Staphylococcus* (wells 6 to 15). The well T(−) corresponds to a negative control tube.

The following examples are given by way of illustration and are in no way limiting. They will enable the invention to be better understood.

1/Culturing the bacteria: 31 bacterial species belonging to the genus *Staphylococcus* as well as 11 bacterial species which did not belong to the genus *Staphylococcus* (Table 1) were cultured on trypcase-soya agar medium by incubating at 37° C. for one night. The collection nos. of the bacterial species which were cultured are given in Table 1 below (ATCC: American type culture collection; DSM: Deutsche Sammlung von Mikroorganismen [German collection of microorganisms]; CCM: Czech collection of microorganisms; CCUG: Culture collection, university of Gothenburg, Sweden).

TABLE 1

Genus and species of the bacteria which were tested in the method according to the invention

| Genus | Species | Collection No. |
| --- | --- | --- |
| *Staphylococcus* | *arlettae* | ATCC43957 |
| *Staphylococcus* | *aureus.aureus* | ATCC25923 |
| *Staphylococcus* | *aureus.aureus* | ATCC35844T |
| *Staphylococcus* | *auricularis* | ATCC33753T |
| *Staphylococcus* | *capitis.capitis* | ATCC27840T |
| *Staphylococcus* | *capitis.ureolyticus* | ATCC49325 |
| *Staphylococcus* | *caprae* | ATCC35538T |
| *Staphylococcus* | *carnosus carnosus* | ATCC51365T |
| *Staphylococcus* | *carnosus utilis* | DSM11676T |
| *Staphylococcus* | *chromogenes* | ATCC43764T |
| *Staphylococcus* | *cohnii cohnii* | ATCC29974T |
| *Staphylococcus* | *cohnii urealyticum* | ATCC49330T |
| *Staphylococcus* | *condimenti* | DSM11674T |
| *Staphylococcus* | *delphini* | ATCC49171T |
| *Staphylococcus* | *epidermidis* | ATCC14990T |
| *Staphylococcus* | *equorum* | ATCC43958T |
| *Staphylococcus* | *gallinarum* | ATCC35539T |
| *Staphylococcus* | *haemolyticus* | ATCC29970T |
| *Staphylococcus* | *hominis.hominis* | ATCC27844T |
| *Staphylococcus* | *hominis.novobiosepticus* | CCUG42399T |
| *Staphylococcus* | *hyicus* | ATCC11249T |
| *Staphylococcus* | *intermedius* | ATCC29663T |
| *Staphylococcus* | *kloosii* | ATCC43959T |
| *Staphylococcus* | *lentus* | ATCC29070T |
| *Staphylococcus* | *lugdunensis* | ATCC43809T |
| *Staphylococcus* | *pasteuri* | ATCC51129T |
| *Staphylococcus* | *piscifermentans* | ATCC51136T |
| *Staphylococcus* | *pulvereri* | ATCC51698T |
| *Staphylococcus* | *saprophyticus.bovis* | CCM4410T |
| *Staphylococcus* | *saprophyticus.saprophyticus* | ATCC15305T |

TABLE 1-continued

Genus and species of the bacteria which were tested in the method according to the invention

| Genus | Species | Collection No. |
| --- | --- | --- |
| Staphylococcus | schleiferi.coagulans | CCUG37248T |
| Staphylococcus | schleiferi.schleiferi | ATCC4308T |
| Staphylococcus | sciuri | ATCC29062T |
| Staphylococcus | simulans | ATCC27848T |
| Staphylococcus | vitulinus | — |
| Staphylococcus | warneri * | ATCC27836T |
| Staphylococcus | xylosus | ATCC29971T |
| Escherichia | coli | ATCC11775T |
| Streptococcus | pneumoniae | ATCC33400T |
| Klebsiella | pneumoniae | ATCC13883T |
| Pseudomonas | aeruginosa | ATCC10145T |
| Enterococcus | faecalis | ATCC19433T |
| Enterobacter | cloacae | ATCC13047T |
| Proteus | mirabilis | ATCC29906T |
| Streptococcus | agalactiae | ATCC13813T |
| Citrobacter | freundii | ATCC8090T |
| Salmonella | enteritidis | ATCC13076 |
| Stenotrophomonas | maltophila | ATCC13637T |

A bioMérieux densitometer (ref. 99234) was used to prepare homogeneous suspensions, of approximately $10^8$ CFU/ml, in sterile water from the different bacterial colonies which were cultured. The bacteria which were contained in a volume of 600 µl of each of the suspensions were lyzed mechanically in order to extract their nucleic acid material. The amplifications were performed on these bacterial lysates.

2) Using the polymerase chain reaction (PCR) to amplify a target sequence of bacteria belonging to the genus *Staphylococcus*: in the case of each bacterial strain, a target sequence was amplified by PCR by using a Roche expand high fidelity kit (ref. 11732650). The PCRs were carried out with the aid of the Fast-Start™ kit (Roche Molecular Biochemicals). Each PCR was carried out in a final volume of 50 µl containing MgCl2 (0.25 mM), deoxynucleotide triphosphates (0.25 mM, Roche), 0.3 µM of the amplification primer comprising 20 nucleotide motifs of SEQ ID No. 1 (5' TAACCTAC-CTATAAGACTGG 3') and 0.3 µM of the amplification primer comprising 20 nucleotide motifs of SEQ ID No. 2 (5' TC ACC CCA ATC ATT TGT CCC 3') and 0.05 U of the mixture of expand high fidelity kit polymerases in order to obtain a final reaction volume of 50 µl.

After 4 min at 95° C., 30 PCR cycles were performed. Each cycle comprised a step of denaturation (30 s at 95° C.); a step of hybridizing the amplification primers with the target sequence (30 s at 55° C.); and a step of forming the amplicons (1 min at 72° C.).

A final extension of 7 min at 72° C. terminated the enzymic amplification reaction.

3) Verifying the amplification: The quality of the amplification was verified on a 1.5% agarose gel in 0.5×TBE buffer after staining with ethidium bromide. The fact that the amplicons were of the correct size was verified by the simultaneous migration of a size marker (Smart Ladder, Eurogentec). The presence of bacteria of the genus *Staphylococcus* was confirmed by the presence of a band of the expected size, corresponding to an amplicon of approximately 1.4 kB, whereas no band was observed in the case of the bacteria which did not belong to the genus *Staphylococcus*.

4) Sensitivity of the amplification primers according to the invention: the sensitivity of the primers was tested on genomic DNA. For this, a range of genomic DNA ($2.10^7$; $2.10^6$; $2.10^5$; $2.10^4$; $2.10^3$; $2.10^2$ and $2.10^1$ copies/µl) was prepared for determining the sensitivity of the primers and tested in PCRs using a protocol which was comparable to that described in paragraph 2) of the example. Amplicons were obtained for genomic DNA concentrations which were higher than, or equal to, $2.10^5$ copies/µl.

5) Specificity of the primers: an amplicon of approximately 1400 base pairs was obtained for each of the 39 bacterial species belonging to the genus *Staphylococcus* whereas no amplicon was generated in the case of the other bacterial species which did not belong to the genus *Staphylococcus*, thus demonstrating the very good specificity of the primers according to the invention and, more specifically, of the primer pair according to the invention. As an indication, an example of an electrophoresis gel which was obtained following the migration of different amplicons which were derived from different bacterial species belonging to the genus *Staphylococcus* (*Staphylococcus cohnii* ssp *cohnii*; *Staphylococcus cohnii* ssp *urealyticum*; *Staphylococcus intermedius*; *Staphylococcus xylosus*; *Staphylococcus pasteuri*) and bacterial species which did not belong to the genus *Staphylococcus* (*Streptococcus pneumoniae*; *Klebsiella pneumoniae*; *Pseudomonas aeruginosa*; *Enterococcus faecalis*; *Enterobacter cloacae*; *Proteus mirabilis*; *Streptococcus agalactiae*; *Citrobacter freundii*; *Salmonella enteritidis*; *Stenotrophomonas maltophila*) is shown in FIG. 1.

The amplification yield was assessed on an Agilent 2100 bioanalyzer. A good amplification yield of approximately 18 ng/µl was obtained.

Comparable results were obtained from samples which were taken under clinical conditions (Geneva University Hospital) and which contained the following bacteria: *S. arlettae*; *S. auricularis*; *S. aureus*; *S. capitis*; *S. caprae*; *S. carnosus*; *S. caseolyticus*; *S. chromogenes*; *S. cohnii*; *S. condimenti*; *S. delphini*; *S. epidermidis*; *S. equorum*; *S. felis*; *S. gallinarum*; *S. haemolyticus*; *S. hominis*; *S. hyicus*; *S. intermedius*; *S. kloosii*; *S. lentus*; *S. lugdunensis*; *S. muscae*; *S. pasteuri*; *S. piscifermentans*; *S. pulvereri*; *S. vitulinus*; *S. saccharolyticus*; *S. saprophyticus*; *S. schleiferi*; *S. sciuri*; *S. simulans*; *S. warneri*; *S. xylosus*.

The invention claimed is:

1. A method for detecting a member of the genus *Staphylococcus* in a biological sample, comprising:
   A. extracting a nucleic acid material from the biological sample,
   B. contacting the extracted nucleic acid material with an amplification primer comprising the nucleotide sequence set forth in SEQ ID NO. 1 and/or an amplification primer comprising the nucleotide sequence set forth in SEQ ID No. 2 under amplification conditions, wherein if a target sequence is present in the nucleic acid material, then amplicons of the target sequence are obtained by amplification, and
   C. detecting the amplicons:
   wherein the presence of the amplicons indicates the presence of the member of the genus *Staphylococcus* in the sample and the method detects the following members of the genus *Staphylococcus: Staphylococcus arlettae; Staphylococcus aureus.aureus; Staphylococcus auricularis; Staphylococcus capitis.capitis; Staphylococcus capitis.ureolyticus, Staphylococcus caprae; Staphylococcus carnosus carnosus; Staphylococcus carnosus utilis; Staphylococcus chromogenes; Staphylococcus cohnii cohnii; Staphylococcus cohnii urealyticum; Staphylococcus condimenti; Staphylococcus delphini; Staphylococcus epidermidis; Staphylococcus equorum; Staphylococcus gallinarum; Staphylococcus haemolyticus; Staphylococcus hominis.hominis; Staphylococcus hominis. novobiosepticus; Staphylococcus hyicus; Staphylococcus intermedius; Staphylococcus kloosii; Staphylococcus lentus, Staphylococcus lugdunensis; Staphylococcus pasteuri; Staphylococcus piscifermentans; Staphylococcus pulvereri; Staphylococcus saprophyticus.bovis; Staphylococcus saprophyticus.saprophyticus; Staphylococcus schleiferi.coagulans; Staphylococcus schleiferi.schleiferi; Staphylococcus sciuri, Staphylococcus simulans; Staphylococcus vitulinus, Staphylococcus warneri* and *Staphylococcus xylosus.*

* * * * *